United States Patent
Funatsu et al.

(10) Patent No.: US 6,284,451 B1
(45) Date of Patent: Sep. 4, 2001

(54) CELL CULTURE MODULE HAVING SINUSOID-LIKE STRUCTURE

(75) Inventors: Kazumori Funatsu, 45, Ichinotani 6-chome, Kasuga-shi, Fukuoka 816-0852; Hiroyuki Ijima, Munakata; Kouji Nakazawa; Hiroshi Mizumoto, both of Fukuoka, all of (JP)

(73) Assignees: Toyo Boseki Kabushiki Kaisha, Osaka; Kazumori Funatsu, Kasuga, both of (JP)

( * ) Notice: Subject to any disclaimer, the term of this patent is extended or adjusted under 35 U.S.C. 154(b) by 0 days.

(21) Appl. No.: 09/648,027

(22) Filed: Aug. 25, 2000

(30) Foreign Application Priority Data

Aug. 25, 1999 (JP) .................................................. 11-238818
Jun. 22, 2000 (JP) .................................................. 12-188275

(51) Int. Cl.$^7$ ...................................................... A61F 2/04
(52) U.S. Cl. .......................... 435/1.1; 435/370; 435/400; 435/405; 435/387; 210/321.89; 604/6; 623/12
(58) Field of Search ..................................... 435/370, 400, 435/405, 387, 1.1; 623/12; 210/321.89; 604/6

(56) References Cited

U.S. PATENT DOCUMENTS

| 5,043,260 | * | 8/1991 | Jauregui ..................................... 435/1 |
| 5,516,691 | | 5/1996 | Gerlach . |

FOREIGN PATENT DOCUMENTS

| 06 57141 | 8/1994 | (JP) . |
| 06 69364 | 9/1994 | (JP) . |
| 07 46988 | 5/1995 | (JP) . |
| 09 56814 | 3/1997 | (JP) . |
| 10 29951 | 2/1998 | (JP) . |
| 10 33671 | 2/1998 | (JP) . |

OTHER PUBLICATIONS

Nyberg et al., "Evaluation of a Hepatocyte–Entrapment Hollow Fiber Bioreactor: A Potential Bioartificial Liver," Biotechnology and Bioengineering, 41(2), pp. 194–203 (Jan. 20, 1993).

Rozga et al., "Development of a Bioartificial Liver: Properties and Function of a Hollow–fiber Module Inoculated with Liver Cells," Hepatology, 17 (2), pp. 258–265 (Feb. 1993).

Sussman et al., "Reversal of Fulminant Hepatic Failure Using an Extracorporeal Liver Assist Device," Hepatology, 16 (1), pp. 60–65 (1992).

Matsushita et al., "High Albumin Production by Multicellular Spheroids of Adult Rat Hepatocytes Formed in the Pores of Polyurethane Foam," Applied Microbiology and Biotechnology, 36, pp. 324–326 (1991).

Funatsu, "Development of Hybrid Artificial Liver Using Hollow Fiber," Abstracts of the 31st Summer Seminar of the Society of Fiber Science and Technology, Japan, pp. 115–118 (Sep. 4, 2000).

Katori et al., "Development of Hybrid Artificial Liver Having Sinusoid–Like Structure," Abstracts of the 33rd Autumn Meeting of the Society of Chemical Engineers, Japan (Aug. 12, 2000).

Mizumoto et al., "Development of Hybrid Artificial Liver Having Sinusoid–Like Structure," Abstracts of the Year 1999 Academic Seminars of Kyushu Branch of the Japan ME Society, p. 22 (Mar. 4, 2000).

Mizumoto et al., "Development of Hybrid Artificial Liver Incorporating Sinusoid–Like Structure," Abstracts of the 32nd Autumn Meeting of the Society of Chemical Engineers, Japan, N202 (Aug. 26, 1999).

* cited by examiner

*Primary Examiner*—James Ketter
(74) *Attorney, Agent, or Firm*—Leydig, Voit & Mayer, Ltd.

(57) ABSTRACT

The present invention provides a module for cell culture comprising a structure comprising hollow fibers and at least two spacers, wherein the spacers have small pores regularly arranged therein and the hollow fibers pass through the small pores and are arranged regularly at a very small distance, a hybrid artificial liver module wherein hepatocytes are immobilized in this module, and a method of cell culture wherein cells are immobilized in the lumen or extra-fiber space of the module by the use of a centrifugal force and wherein the immobilized cells are cultured. The present invention also provides a method for cell culture wherein hepatocytes are cultured in a culture medium containing DMEM as a basal medium.

20 Claims, 9 Drawing Sheets

CELL CULTURE MODULE HAVING SINUSOID-LIKE STRUCTURE

FIELD OF THE INVENTION

This invention relates to a method for forming a multicellular aggregate applicable to the production of useful cellular products by the use of animal cells or a hybrid (or biological) artificial organ, and to a module into which the multicellular aggregate has been incorporated. More particularly, this invention relates to a technique for inducing the formation of an aggregate of cultured cells by the use of a centrifugal force, as a method for forming a multicellular aggregate which can maintain the cells for a long time without losing their inherent functions, to a module for cell culture which reproduces a sinusoid-like structure of a living body by the use of hollow fibers, and to a method for cell culture using the module and the aggregate inducing technique in combination.

This invention further relates to a culture medium suitable for culturing the multicellular aggregate and a culture method of the multicellular aggregate using the medium.

BACKGROUND OF THE INVENTION

Culture devices for multiplying animal cells for the production of useful cellular products, or for using the cells as a component of a hybrid artificial organ, have been conventionally known. Such known culture devices employ agitation tank culture using a micro carrier for high-density culture of cells (W. R. Tolbert et al., Ann. Rep. Ferment. Proc., 6, 35 (1983), etc.), flow bed or fixed bed culture using a porous carrier (JP 7-46988 B, etc.), and culture using a porous hollow fiber membrane to immobilize cells in the lumen or the extra-fiber space (Naka et al., Artificial Organs, 28(1), 68–73 (1999), etc.). Of these, the culture using a hollow fiber membrane is superior in that it provides the protection against shear stress and prevention of leakage, because the cells are separated from the flow of a medium by the hollow fiber membrane. In addition, existing dialysis devices and plasma separation devices can be used as the culture device to be applied to the hollow fiber membrane, because they contain a multitude of hollow fibers in a bundle. In such hollow fiber type culture device, however, the hollow fibers are not uniformly arranged within the culture tank (module). This in turn poses a problem in that, when cells are to be immobilized in the extra-fiber space of the module, the distance of mass transfer to the surface of the hollow fibers differs depending on the position in the module, thereby producing variation in the viability and growth of the cells.

The anchorage-dependent animal cells have been dominantly cultured by a two-dimensional monolayer culture method. This method is associated with a problem in that the cultured cells rapidly lose functions. For example, highly differentiated primary hepatocyte loses its functions during several days of culture under the monolayer culture conditions. In view of such defects, an attempt has been made to develop a cell aggregate culture for the expression and maintenance of highly differentiated functions. For example, culture of spherical multicellular aggregate (spheroid) of cultured cells using a porous polyurethane foam (PUF) has been utilized in the development of a hybrid artificial liver required to express high functions (Matsushita et al., Artificial Organs, 21(3), 1050–1054 (1992)).

When an aggregate is contained in a module, the cell aggregate has an extremely high cell density sufficient to enable high-density culture of the cells, which in turn reduces the size of the module. On the other hand, the consumption of oxygen and nutrients in the module is also striking. When cells with high oxygen consumption, such as primary hepatocytes, are to be cultured, conventional devices allow only the cell density of about $1\times10^7$ cells/cm$^3$, because insufficient supply of oxygen and nutrients for the culture of the highly dense cells results in necrosis of the cells in the aggregate, demonstrating degraded function of the device. Due to such problems, it is difficult for the cells to maintain viability for a long time under the high-density culture conditions without impairing inherent cell functions.

For the maintenance of the functions of the primary hepatocytes, the importance of the composition of the culture medium has been emphasized along with the importance of cell morphology, and there have been documented reports on culture media containing various supplemental factors. For example, there are reports on enhanced viability of hepatocytes by the addition of high concentration L-alanine to a culture medium (JP 5-336959 A), maintenance of albumin secretion by hepatocytes by the use of a culture medium containing ascorbic acid (JP 7-274952 A), maintenance of albumin secretion by spheroid culture hepatocytes for about 60 days by the use of William's E medium (WEM) supplemented with dexamethasone, glucagon, insulin and the epidermal growth factor (EGF) (J. Z. Tong et al., Exp. Cell Res., 189, 87–92, 1990), maintenance of albumin secretion ability of collagen sandwich culture hepatocytes for about one month by the use of Dulbecco's modified Eagle's medium supplemented with proline, insulin, glucagon, hydrocortisone and EGF (J. Lee et al., Biotech. Bioeng., 40, 298–305, 1992), and others.

However, maintenance of the function of detoxifying foreign compound, ammonia produced in the body and drug, as possessed by the hepatocytes in addition to the protein (e.g., albumin) synthesizing ability, is not feasible, where the ammonia metabolizing ability can be maintained in a conventional culture for only about 2 weeks.

SUMMARY OF THE INVENTION

It is therefore an object of the present invention to provide a method for forming an aggregate that allows various animal cells to survive for a long time without losing their inherent functions, as well as a module incorporating such aggregate at high density, which module is useful for the production of advantageous cellular products and is applicable to a hybrid artificial organ.

Another object of the present invention is to provide a culture medium suitable for a long-term maintenance of various physiological functions, particularly at least ammonia metabolizing ability in addition to the albumin secretion ability, of primary hepatocytes in an artificial liver.

A further object of the present invention is to provide a culture technique that can be applied to a hybrid artificial liver and as an alternative method of animal experiments (safety test of drug etc. on cells instead of animals for protection of animals) over an extended period of time by the use of this medium.

The present inventors have found that a multicellular aggregate having high functions can be formed by forcibly immobilizing cells in the lumen or extra-fiber space of the module, or in other culture substratum, by the aid of centrifugal force, thereby to increase the contact frequency between cells. They have also found that a tissue-like structure can be constructed by immobilizing cells at high density in the extra-fiber space or lumen of hollow fibers having a semipermeable membrane, and supplying, via the hollow fiber membrane, oxygen and nutrients necessary for the survival of the cells, wherein the hollow fibers constitute a module incorporating a sinusoid-like structure similar to the biological capillary network, together with at least two spacers having small pores regularly formed therein, the hollow fibers passing through the small pores of the spacers to provide a structure comprising hollow fibers arranged regularly at a very small distance. It has been also found that the use of DMEM rich in amino acid, vitamins and energy source, or a mixture of about 60 to 90% DMEM and about 10 to 40% of other medium, supplemented with proline, EGF, insulin, hydrocortisone, selenious acid, linoleic acid, copper sulfate and zinc sulfate for the culture of liver multicellular aggregate leads to a marked elongation of the maintenance of the typical functions of primary hepatocytes including the ammonia metabolizing ability.

When this medium is used in combination with the above-mentioned module and the method for forming a multicellular aggregate, a hybrid artificial liver can be made, that enables maintenance of the typical functions of primary hepatocytes inclusive of an ammonia metabolizing ability for at least 4 months.

Accordingly, the present invention provides a module for cell culture, which comprises at least two spacers having small pores regularly formed therein, through which hollow fibers pass and are arranged regularly at a very small distance. Such structure is similar to the capillary network in the living body, and, upon efficient supply, via the hollow fiber membrane, of oxygen and nutrients necessary for the survival of the cells immobilized in the extra-fiber space and/or lumen of the hollow fibers, promotes formation of a multicellular aggregate having high physiological functions, and contributes to the maintenance of various physiological functions of the multicellular aggregate.

In one aspect of the present invention, a cell culture method is provided, which comprises immobilizing cells in the lumen of a hollow fiber, or the lumen or extra-fiber space of a hollow fiber in a module for cell culture, by the aid of a centrifugal force, and culturing the immobilized cells. By the application of the centrifugal force, the cells aggregate to increase contact frequency, thereby promoting formation of multicellular aggregates.

In another aspect of the present invention, a culture method of hepatocytes is provided, which can maintain the typical functions of primary hepatocytes, inclusive of detoxifying function, for a long time by the use of DMEM or a mixture of DMEM and other medium as a basal medium. When proline, EGF, insulin, hydrocortisone, selenious acid, linoleic acid, copper sulfate and zinc sulfate are added to the DMEM or mixed medium containing DMEM, the hepatocyte functions can be maintained for an extended period of time. The present invention also provides a culture medium containing DMEM and the above-mentioned supplements.

As stated in the foregoing, by utilizing the centrifugal force, the cultured cell aggregate induction technique of the present invention has enabled formation of an aggregate that can maintain high functions for a long time, as compared to conventional culture methods.

Combined with the module having a sinusoid-like structure comprising hollow fibers regularly arranged therein, moreover, the present invention provides a markedly high density culture as compared to conventional modules for cell culture. Moreover, a hybrid artificial liver that maintains not only the protein synthesis ability but also the detoxifying function inclusive of ammonia metabolizing ability for a long time can be provided by culturing the hepatocytes in a culture medium containing DMEM as a basal medium, in a hybrid artificial liver module prepared by combining the aggregate induction technique and the module of the present invention. Therefore, the present invention affords conventionally unfeasible development of a highly functional, small module for cell culture, which is utilizable as a hybrid artificial organ and for the production of useful cellular products.

BRIEF DESCRIPTION OF THE DRAWINGS

In the above Figures, 1 shows a housing, 2 shows a hollow fiber, 3 shows a spacer, 4 shows a sealing part, 5 shows an extra-fiber space, 6 shows a cell inlet, 7 shows a medium flow inlet, 8 shows a medium flow outlet, 9 shows a small pore in the spacer and 10 shows a multicellular aggregate.

DETAILED DESCRIPTION OF THE INVENTION

In the following, a method for forming a cell aggregate by the use of a centrifugal force is explained in detail. When a suitable centrifugal force is applied to a cell suspension, the cells sediment due to the centrifugal force to form a cell aggregate. The cells are in a densely packed state at this stage, with an extremely high contact frequency between cells. When oxygen and suitable nutrients are supplied to the cells in this state, an aggregate can be formed, wherein the cells can express high functions for a long time. For example, hepatocytes are highly densely immobilized in the lumen of a hollow fiber having a semipermeable membrane, by the aid of a centrifugal force, and oxygen and nutrients are supplied from the outside of the hollow fiber and the metabolic excreta are removed. As a result, the cells form a cylindrical aggregate in the hollow fiber lumen. The high-density immobilization of the cells by the application of a centrifugal force is not restricted to the hollow fiber lumen. When, for example, the hollow fibers are regularly arranged as mentioned below, the cells can be immobilized in the extra-fiber space between hollow fibers. In any case, the cells can form a tissue-like structure in an environment where the cells can survive.

The centrifugal force is set to a level within the range where the cells to be used are free of damage. In the case of primary rat hepatocytes, the centrifugal force is preferably, but not limited to, not more than 1500×G, more preferably from 5×G to 400×G. The centrifugation time can be also set according to the centrifugal force.

The hollow fiber to be used to form a multicellular aggregate in the present invention by the application of a centrifugal force is subject to no particular limitation as long as it has a semipermeable membrane structure. The inner diameter thereof is preferably about 20–1000 μm, more preferably about 50–500 μm, most preferably about 50–150 μm. The module for cell culture to be used for forming the multicellular aggregate in the present invention is subject to no particular limitation as long as it has a hollow fiber membrane. In a preferable mode, a module for cell culture to be mentioned below is used, which has a structure wherein the fibers are regularly arranged at a very small distance.

Figure 1:
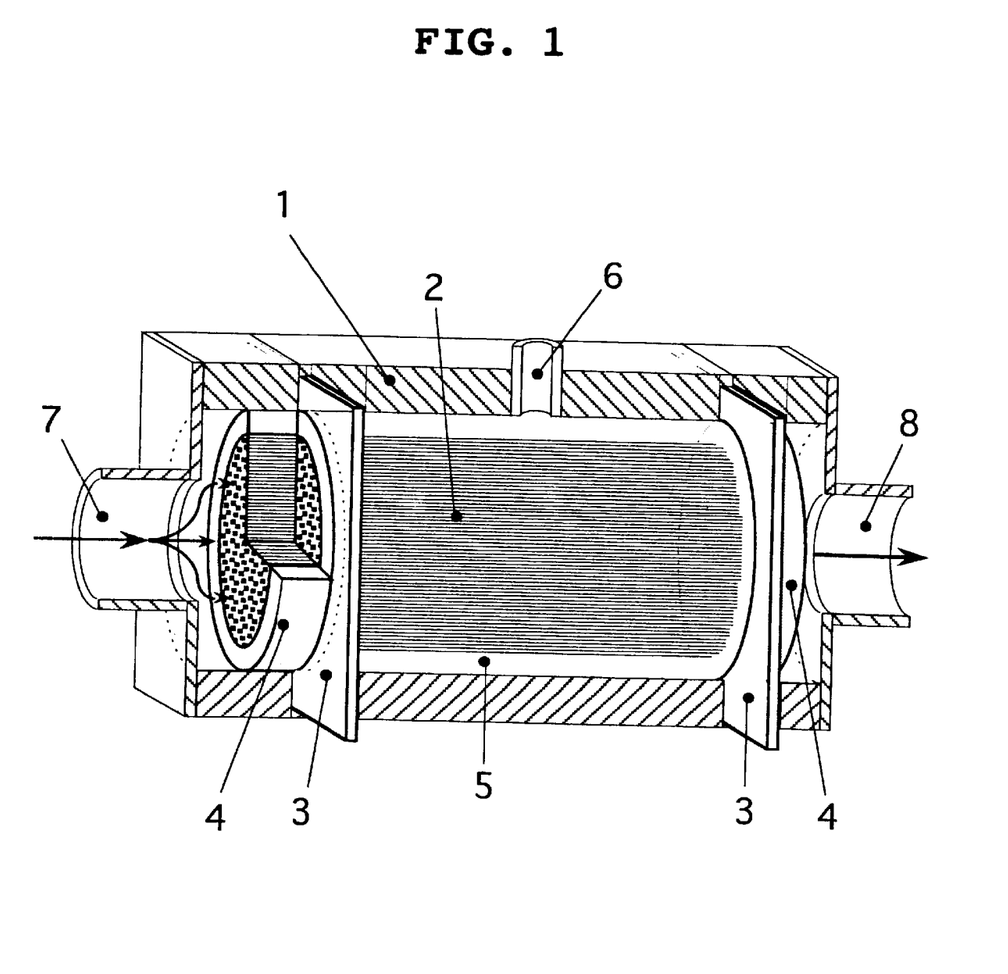
FIG. 1 shows an example of the inventive hollow fiber type module.
Figure 2A:
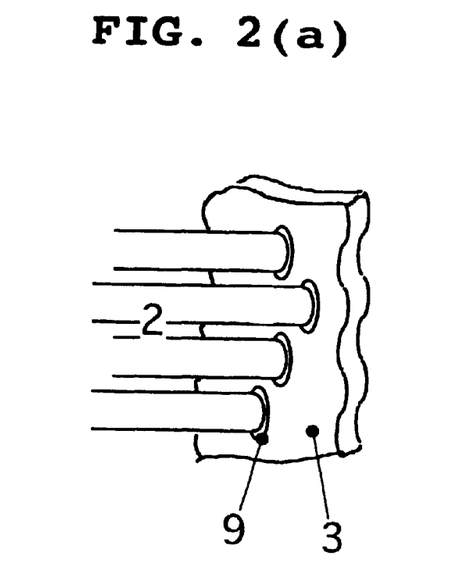
FIG. 2(a) is an enlarged view of the vicinity of a spacer as shown in FIG. 1.
Figure 2B:
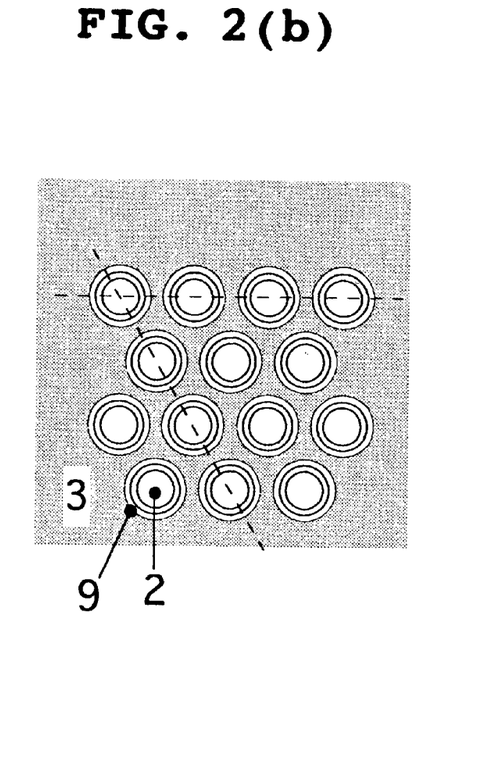
FIG. 2(b) is a cross section of the module in the radius direction.
Figure 3:
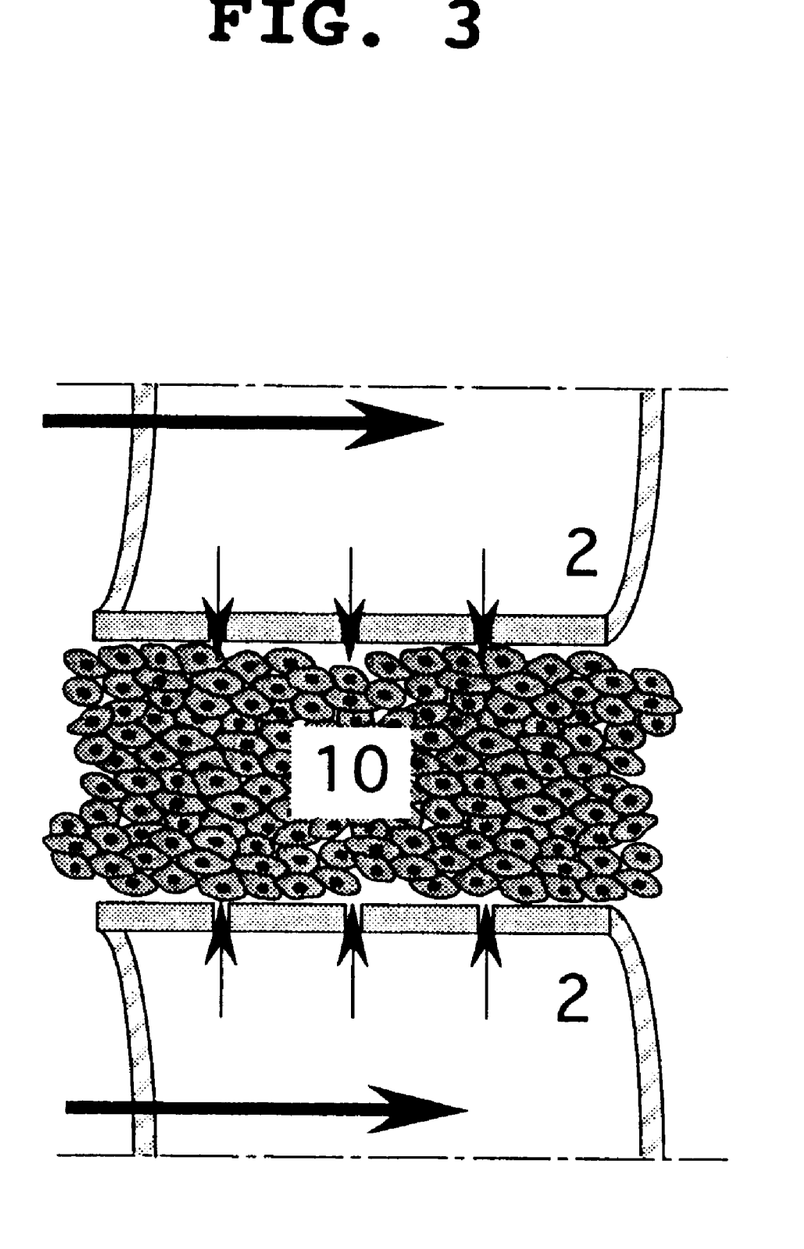
FIG. 3 is a schematic showing of the cells immobilized in the space between hollow fibers in FIG. 1.

A module for cell culture, which incorporates the structure wherein the fibers are regularly arranged at a very small distance (hereinafter to be also referred to as a sinusoid-like structure), is explained in the following. As used herein, by the sinusoid-like structure is meant a structure comprising a multitude of hollow fibers (preferably having the above-mentioned inner diameter) like capillary, regularly arranged at a very small distance of about several hundred micrometers, preferably 20–1000 μm, more preferably 50–500 μm, most preferably 50–150 μm. This structure supplies oxygen and nutrients to the cells present in the inside or outside of a shell and removes excreta. FIG. 1, FIG. 2 and FIG. 3 show an embodiment of the module for cell culture of the present invention.

The method for forming a module as shown in FIG. 1 is explained in the following. The spacers to be used are superimposed on one another such that the small pores on the spacers match and hollow fibers are passed through the matched small pores. When the hollow fibers are passed therethrough, the spacers are extended for a desired distance and fixed at given positions in a housing 1. The hollow fibers are fixed by a sealing part 4. The sealing part can be formed by injecting a potting agent with a centrifugal force into a given part, and after curing of the potting agent, the cured part is cut with a sharp blade to expose the opening of the hollow fiber.

In FIG. 1, a sinusoid-like structure consisting of an appropriate number of hollow fibers 2 is set in a housing 1. Each hollow fiber constituting the sinusoid-like structure passes through a small pore 9 of a spacer 3 and is fixed by the sealing part 4. That is, each hollow fiber 2 is uniformly set in a space 5 at a distance between the small pores 9 in the spacers 3 set in the number of two or more as shown in FIG. 2.

When the cells are immobilized in the extra-fiber space in a module of this constitution, the cells 10 fed from a cell inlet 6 formed in the housing 1 at one or more positions are immobilized by the action of a centrifugal force, at high density around each hollow fiber set in the space 5. The culture medium is dispersed from a culture medium flow inlet 7 on each hollow fiber constituting the sinusoid-like structure and, as shown in FIG. 3, supplies oxygen and nutrients to the cells 10 immobilized in the space 5, recovers the product and metabolic excreta of the cells and is drained from the module through a culture medium flow outlet 8.

It is also possible to impart an independent function of culture medium supply or drain to the regularly arranged hollow fibers. That is, a hollow fiber for culture medium supply has one closed end at the sealing part 4 and the culture medium that is fed into the module through this part is forcibly sent into the space 5, where it comes into direct contact with the cells 10, and after exchange of various substances, is drained to the outside of the module through the hollow fiber for culture medium drain. Similarly, a hollow fiber can be set as an independent pipeline for oxygen supply.

In this constitution, the hollow fibers for supply of oxygen and nutrients, and for the recovery of the product and metabolic excreta of the cells, are arranged at a very small distance in the module, thus reproducing, in the module, the micro sinusoid in the living body. By immobilizing the cells at a high density around the hollow fibers by the application of the centrifugal force and culturing the cells, an aggregate of cells having high functions can be formed. The cells immobilized by the centrifugal force have a density of from about $1 \times 10^7$ to $1 \times 10^9$ cells/ml, though subject to variation depending on the cell type and the centrifugal force to be applied. When the cells are placed in such a high density state, or when they form an aggregate, the substance to be supplied, which highly likely becomes a limiting factor, is oxygen, and the distance between the hollow fibers in a hollow fiber bundle 2 can be determined in consideration of the oxygen consumption of the cells immobilized in the space 5. This can be achieved by controlling the distance between the small pores 9 formed in the spacer 3. To be specific, the distance between hollow fibers is preferably 20–1000 μm, more preferably 50–500 μm, most preferably 50–150 μm. The distance is determined in consideration of the oxygen consumption of the cells and is not limited to the above range.

The small pore 9 set in the spacer 3 can have a diameter appropriately set according to the diameter of the hollow fiber to be used. The diameter is preferably greater by about 20–100 μm than the diameter of the hollow fiber to be used, but is not limited to this range. In addition, the spacers 3 are generally set in adjacency with the both sealing parts 4 of the hollow fiber bundle 2, but may be additionally set in the space 5 where necessary. For example, when the hollow fiber is longer, a few spacers 3 may be added in the space 5 to make the hollow fibers more regularly arranged.

When the hollow fiber is long, a shaft having a smaller diameter than the inner diameter of the hollow fiber may be passed through the hollow fiber to prevent sagging of the hollow fiber between two spacers. When a shaft is used, the material of the shaft is free of any particular limitation as long as it has superior biocompatibility, with preference given to one having a smooth outer surface, that avoids damage on the inside of the hollow fiber, and a relatively high strength.

The small pores 9 formed in the spacer 3 may be aligned to form a triangular arrangement, and so are the hollow fibers, to efficiently culture the cells immobilized in the space 5, but can also form a rectangular arrangement or other shape.

The hollow fiber that exchanges substances with the cells has an inner diameter free of any particular limitation. It is preferably about 20–1000 μm, more preferably about 50–500 μm, most preferably about 50–150 μm. The hollow fiber has a membrane thickness of about 10–200 μm. The material of the hollow fiber is free of any particular limitation as long as it does not act adversely on the cell or body fluid. For example, cellulose materials, polysulfone, polypropylene and the like are used. In view of the material exchangeability, the average pore diameter of the porous hollow fiber membrane is desirably greater, and is about 0.1–5 μm. The pore diameter is not limited to this range, but can be set appropriately according to the object of use. For example, when plasma is introduced into the module, a membrane having a smaller fractionated molecular weight, having a pore diameter of less than 0.1 μm, may be used to suppress a heterologous immune reaction.

The module has the above constitution when the cells are immobilized in the outside space of the hollow fiber. It is also possible to immobilize cells in the hollow fiber lumen with a centrifugal force. In this case, the cells are immobilized in the hollow fiber lumen with a centrifugal force and the both ends of the hollow fiber are closed. The culture medium flows outside the hollow fiber and exchanges substances with the cells via the hollow fiber membrane. A housing 1 has two or more ports for the flow of culture medium.

The material of the module is free of any particular limitation as long as it is superior in the biocompatibility. Any material conventionally used for the artificial dialysis device, plasma separation device and the like can be used. An adhesive to be used for the sealing part 4 to fix the hollow fibers and separate the cells in the culture device from the circulating fluid may be a conventional one. For example, polyurethane, silicone and epoxy resin can be used.

In the present invention, the cells to be cultured are free of any particular limitation as to the kind and the origin of the cells. The cells may be originated from human, mouse, rat or any other animals. In particular, when hepatocytes are immobilized in a module having a sinusoid-like structure by the action of the above-mentioned centrifugal force, a compact hybrid artificial liver module that can maintain high functions for a long time can be prepared, unlike the conventional hybrid artificial liver.

In the present invention, the cells are immobilized with a centrifugal force to give a three dimensional multi-layer of cells in a fine viable state, because of the small shear stress applied during cell immobilization. Moreover, the regularly arranged hollow fibers (the space outside the hollow fiber when cells are immobilized in the hollow fiber lumen) function as a capillary in the living body, thereby allowing fine substance exchange with the cells. The hollow fiber can be arranged in such a manner that substance exchange is available with every cell in the space. This in turn makes it possible to place the cells in a very small space imitating inside the living body, at the cell density ($1 \times 10^8 - 10^9$ cells/$cm^3$) comparable to the inside of a living tissue. Consequently, the cells immobilized at high density by the use of a centrifugal force form an aggregate without cell necrosis in an early stage of culture. Therefore, the cells can be applied to various uses as a hollow fiber culture module in which the cells can survive without losing inherent functions during culture of various animal cells. Specific fields of application include hybrid artificial organs, such as hybrid artificial liver and hybrid artificial pancreas, that are produced utilizing cultured cells, organ simulator utilizing cultured cells for the analysis of drug metabolism and the like, and bioreactor utilizing cultured cells for the production of useful cellular products.

The present invention also provides a hepatocyte culture method that permits maintenance of typical functions of the primary hepatocyte for a long time for the culture of a hybrid artificial liver utilizing the module for cell culture and multicellular aggregate formation technique of the present invention, which comprises the use of DMEM or a mixed medium of DMEM and other medium as a basal medium. As used herein, by the typical functions of the primary hepatocyte is meant detoxifying functions inclusive of at least ammonia metabolizing ability in addition to the albumin secretion ability.

The other medium to be mixed with DMEM in the present invention is a medium conventionally used as a basal medium for the culture of animal cells, and is free of any particular limitation as long as it does not inhibit the effect of long term maintenance of primary hepatocyte functions by DMEM or as long as it increases the effect. For example, Ham's F-10 medium, F-12 medium, William's E medium, MCDB153 medium, RPMI-1640 medium, 199 medium, L-15 medium and the like can be used. Preferred are Ham's F-12 medium, William's E medium, MCDB153 medium, RPMI-1640 medium and the like. The mixing ratio of DMEM and other medium can be appropriately set within the range free of an adverse influence on the effect of the DMEM or conducive to the effect. The basal medium of the present invention is preferably a mixed medium containing about 60–about 90% DMEM and about 10–about 40% other medium.

The medium to be used for the above-mentioned hepatocyte culture method may contain any supplements besides DMEM or the above-mentioned DMEM-containing mixed medium. Preferably, it contains proline, EGF, insulin, hydrocortisone, selenious acid, linoleic acid, copper sulfate and zinc sulfate as supplements. Thus, the present invention also provides a medium containing DMEM or a mixed medium of DMEM and other medium, as a basal medium, and proline, EGF, insulin, hydrocortisone, selenious acid, linoleic acid, copper sulfate and zinc sulfate as additional components. This medium can be advantageously used for the hepatocyte culture using the module for cell culture and the multicellular aggregate formation technique of the present invention in combination. Moreover, the medium can be used for conventional hepatocyte culture and for other typical culture of animal cells and tissues.

The concentrations of proline, EGF, insulin, hydrocortisone, selenious acid, linoleic acid, copper sulfate and zinc sulfate to be contained in the culture medium of the present invention are free of any particular limitation as long as they do not prevent the effect of DMEM used in the hepatocyte culture method of the present invention. Preferably, the concentrations are conducive to the significant enhancement of the effect of DMEM in the hepatocyte culture method of the present invention. As used herein, by the effect of DMEM is meant an effect to maintain detoxifying functions including at least ammonia metabolizing ability of hepatocyte for a long time, besides the albumin secretion ability. For example, each component to be added preferably has a concentration of 0.1–1000 mg/L for proline, $1-1\times10^6$ ng/L for EGF, $1-1\times10^9$ ng/L for insulin, $1-1\times10^5$ μg/L for hydrocortisone, $0.1-10^5$ nM for selenious acid, $0.1-1\times10^6$ μg/L for linoleic acid, $1-1\times10^6$ nM for copper sulfate, and $0.1-1\times10^9$ pM for zinc sulfate.

The culture medium of the present invention may contain other medium components besides the above-mentioned supplements, as long as they do not inhibit the effect of DMEM in the hepatocyte culture method of the present invention. The medium components to be additionally contained can be selected from the supplemental factors conventionally known.

The present invention is explained in more detail in the following by referring to examples. The present invention is not limited by these examples in any way.

EXAMPLE 1

The primary rat hepatocytes ($5 \times 10^5$ cells) prepared by the collagenase perfusion method were immobilized in the lumen of a cellulose triacetate hollow fiber for plasma separation (manufactured by Toyo Boseki, AP250N15 type; inner diameter 285 μm, outer diameter 387 μm) by centrifugation at 60×G for 90 sec. At this stage, the hepatocyte density in the hollow fiber lumen was $4.5 \times 10^7$ cells/cm$^3$. Five hollow fibers (length 3 cm) containing the hepatocytes were placed in a 35 mm diameter culture dish (manufactured by Iwaki Glass) and 2 ml of a serum-free medium (Hormonally defined medium; HDM) was added, which had been obtained by adding 50 ng/ml EGF (manufactured by Funakoshi), 10 mg/L insulin (manufactured by Sigma), 0.1 μM copper sulfate 5 hydrate (manufactured by Wako Pure Chemical Industries, Ltd.), 3 μg/L selenious acid (manufactured by Wako Pure Chemical Industries, Ltd.), 50 pM zinc sulfate 7 hydrate (manufactured by Wako Pure Chemical Industries, Ltd.), 50 μg/L linoleic acid (manufactured by Sigma), 58.8 mg/L penicillin (manufactured by Meiji Seika), 100 mg/L streptomycin (manufactured by Meiji Seika), 1.05 g/L sodium hydrogencarbonate (manufactured by Wako Pure Chemical Industries, Ltd.) and 1.19 g/L HEPES (manufactured by Dojindo Molecular Technologies, Inc.) to William's E medium (WEM; 10.8 g/L, manufactured by Sigma). The hepatocytes were rotation cultured at 45 rpm on a shaker under the atmosphere of 5% carbon dioxide and 95% air. The liver specific functions were evaluated in terms of metabolizing activity by adding 1 mM ammonia to the culture medium and quantitatively measuring the time course variation in the concentration. In addition, albumin secretion activity was assayed by quantitatively measuring the albumin concentration in the medium.

Figure 4:
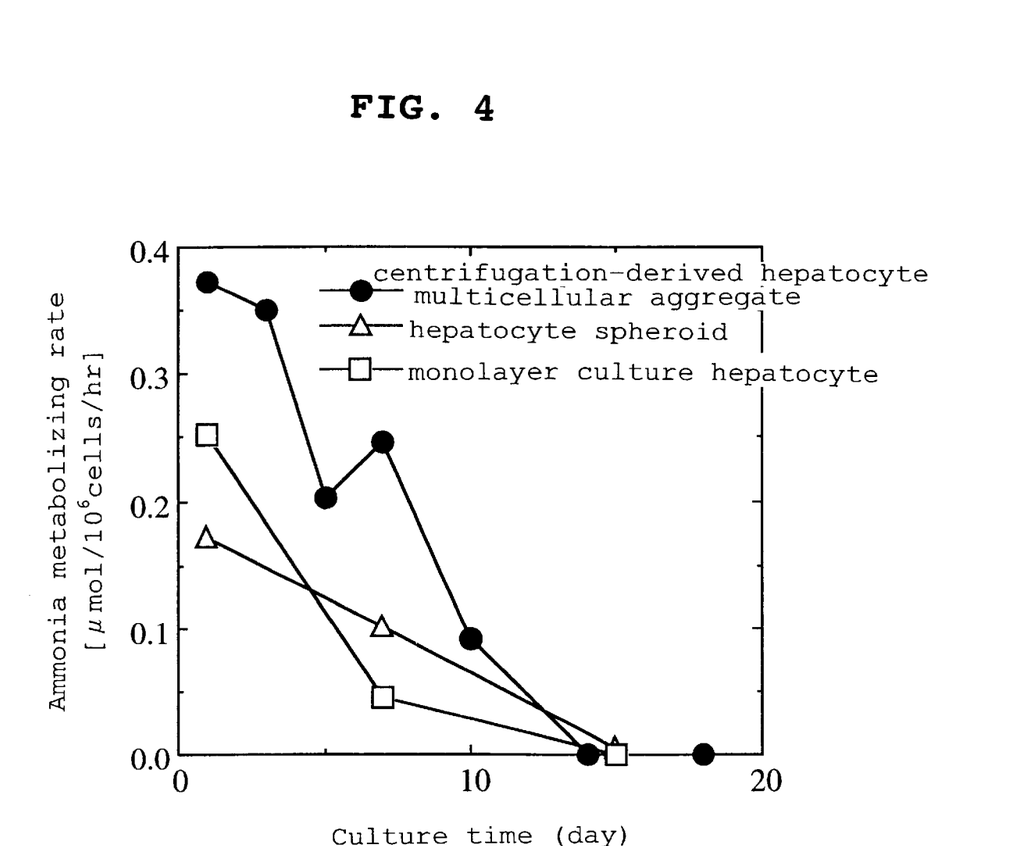
FIG. 4 shows an ammonia metabolizing activity per unit cells of the centrifugation-derived hepatocyte multicellular aggregate of the present invention.

As a control, hepatocytes ($3.0 \times 10^6$ cells) were inoculated in a 25 mm×25 mm×1 mm polyurethane foam (PUF) plate and cultured in a 35 mm diameter culture dish. The hepatocytes ($2.5 \times 10^5$ cells) were seeded on a 35 mm diameter collagen-coated dish (manufactured by Iwaki Glass) and monolayer cultured, which was followed by comparison of the functions. FIG. 4 shows the time course changes in the ammonia metabolizing rate per unit cells.

Figure 5:
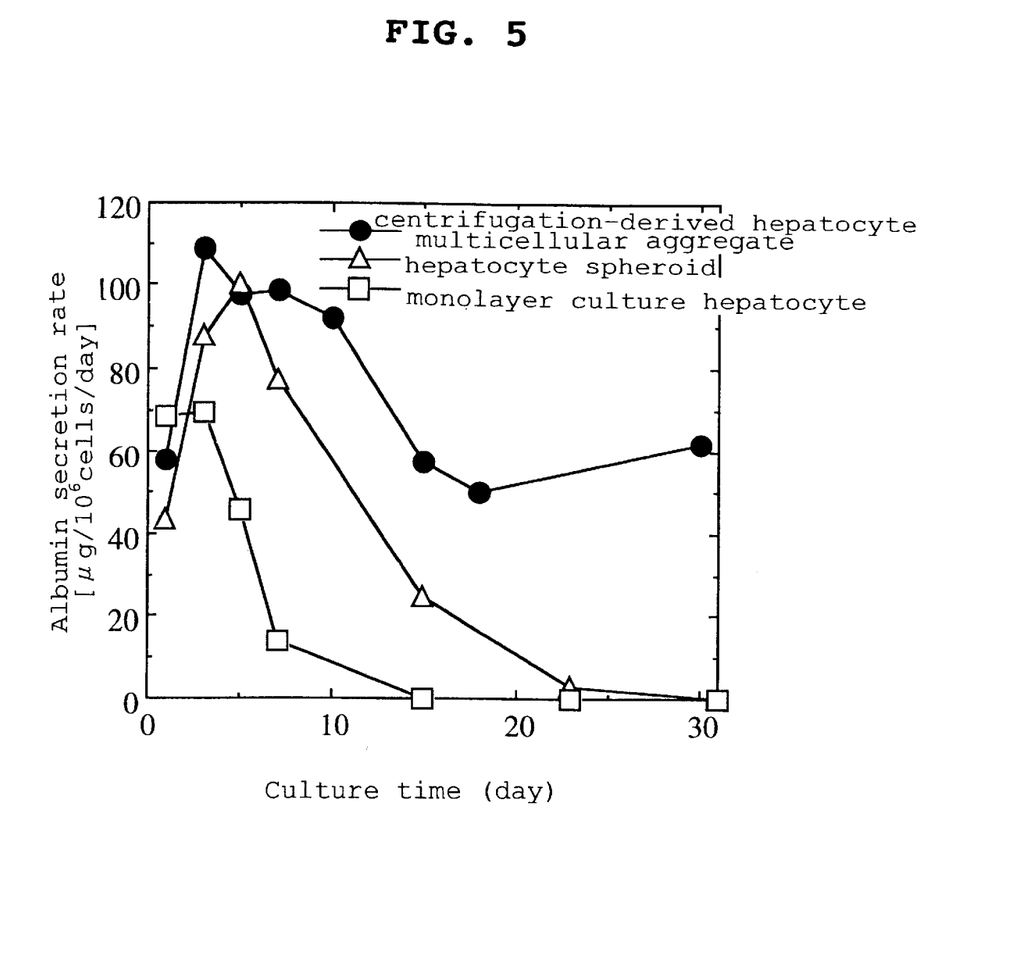
FIG. 5 shows an albumin secretion activity per unit cells of the centrifugation-derived hepatocyte multicellular aggregate of the present invention.

The results reveal that the formation of the centrifugation-derived hepatocyte multicellular aggregate led to a higher ammonia metabolizing activity which was maintained for 2 weeks of culture, as compared to conventional culture methods. FIG. 5 shows the time course changes in the albumin secretion rate per unit cells. The results reveal that the centrifugation-derived hepatocyte multicellular aggregate can maintain albumin secretion activity for a long time, as compared to aggregates formed by conventional culture methods, thereby demonstrating the ability of the centrifuge-derived hepatocyte multicellular aggregate to maintain high liver functions for a long time.

EXAMPLE 2

Small pores (diameter 500 μm) were arranged in a module (inner diameter 9 mm, length 27 mm) at a 600 μm pitch to form a triangular arrangement. A module was prepared, which contained 187 hollow fibers used in Example 1 regularly arranged by two such spacers. Primary rat hepatocytes were immobilized by centrifugation at 60×G for 3 min in the extra-fiber space in this module. A culture medium HDM was perfused through the hollow fiber lumen at a flow rate of 30 ml/min. The cell density per unit volume of the module at this stage was $3 \times 10^7$ cells/cm$^3$.

Figure 6:
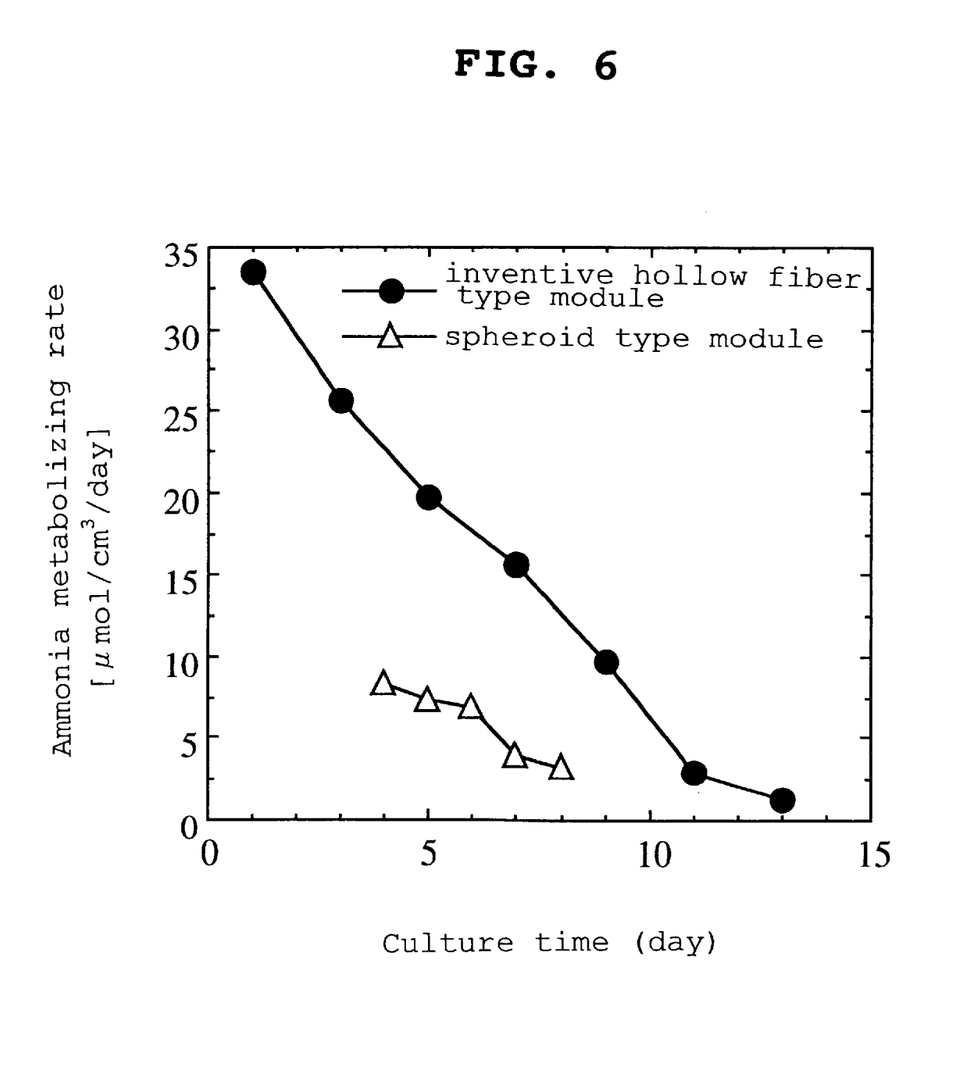
FIG. 6 shows an ammonia metabolizing activity per unit volume of the hollow fiber type module incorporating the aggregate of the present invention.

For the evaluation of the functions of the module, the culture medium was loaded with ammonia at a concentration of 1 mM, and changes in the ammonia concentration and amount of synthesized urea were quantitatively measured to evaluate the ammonia metabolizing activity and urea synthesis activity. FIG. 6 shows the time course changes in the ammonia metabolizing rate per unit volume of the module.

As a control, the activity of the module wherein spheroid had been immobilized in the porous carrier was measured. The module of the present invention showed higher density culture as compared to a spheroid type module incorporating the same hepatocyte multicellular aggregate. The ammonia metabolizing ability per module was about 4 times greater at maximum of the activity than the spheroid type module.

EXAMPLE 3

In the same manner as in Example 1 except that a serum-free medium (medium A) prepared by adding 60 mg/L proline, 50 ng/ml EGF (manufactured by Funakoshi), 10 mg/L insulin (manufactured by Sigma), 7.5 mg/L hydrocortisone (manufactured by Wako Pure Chemical Industries, Ltd.), 0.1 μM copper sulfate 5 hydrate (manufactured by Wako Pure Chemical Industries, Ltd.), 3 μg/L selenious acid (manufactured by Wako Pure Chemical Industries, Ltd.), 50 pM zinc sulfate 7 hydrate (manufactured by Wako Pure Chemical Industries, Ltd.), 50 μg/L linoleic acid (manufactured by Sigma), 58.8 mg/L penicillin (manufactured by Meiji Seika), 100 mg/L streptomycin (manufactured by Meiji Seika), 1.05 g/L sodium hydrogencarbonate (manufactured by Wako Pure Chemical Industries, Ltd.) and 1.19 g/L HEPES (manufactured by Dojindo Molecular Technologies, Inc.) to Dulbecco's modified eagle medium (DMEM; 13.5 g/L, manufactured by Gibco) was used as a culture medium, rat hepatocytes were cultured, and the ammonia metabolizing ability, urea synthesis ability and albumin secretion ability were determined with the lapse of time. To be specific, the culture medium was loaded with ammonia at a concentration of 1 mM and reacted for 24 hours. The amount of ammonia metabolized during the reaction and the synthesized amount of urea were quantitatively measured for the evaluation of each activity. Similarly, the amount of albumin secreted in the medium was quantitatively measured to evaluate the albumin secretion activity.

The same activity evaluation was performed with regard to the hepatocytes cultured using HDM (medium B) containing the same WEM as used in Example 1 as the basal medium, and the long-term maintenance of hepatocyte functions was compared between the two.

Figure 7:
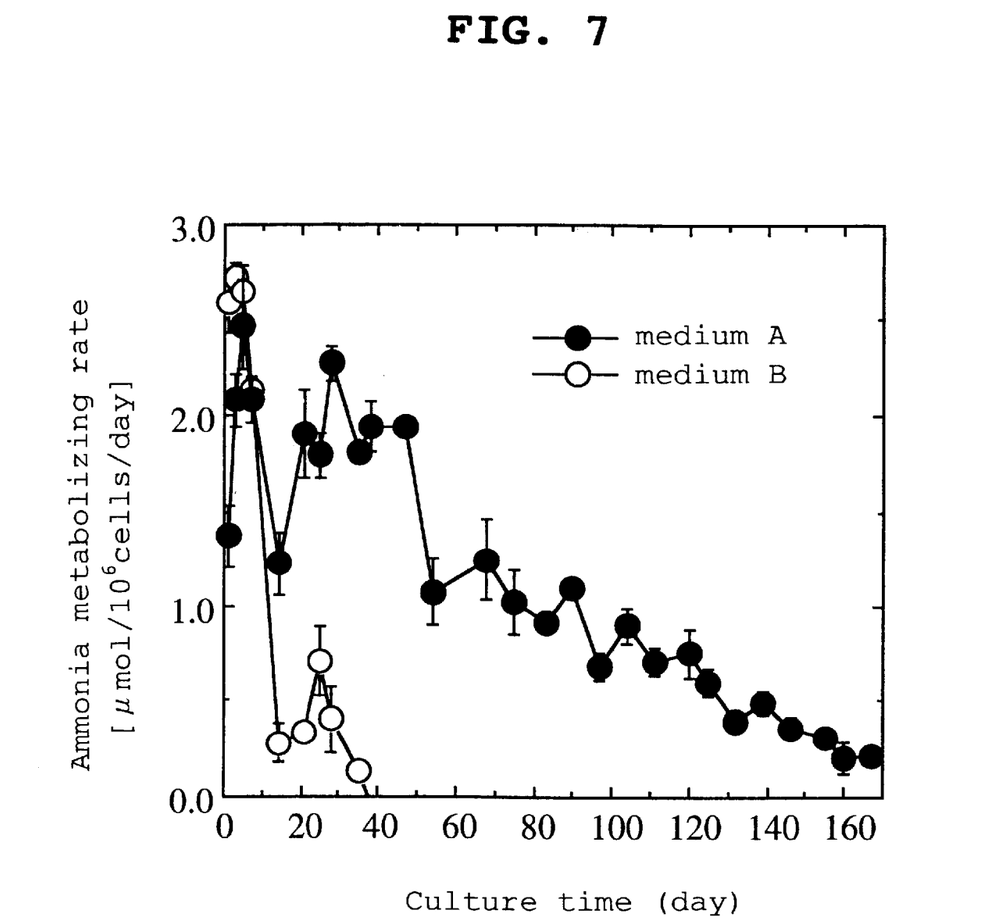
FIG. 7 shows the effect of the composition of the medium on the maintenance of the ammonia metabolizing activity per unit cells of the centrifugation-derived hepatocyte multicellular aggregate of the present invention.
Figure 8:
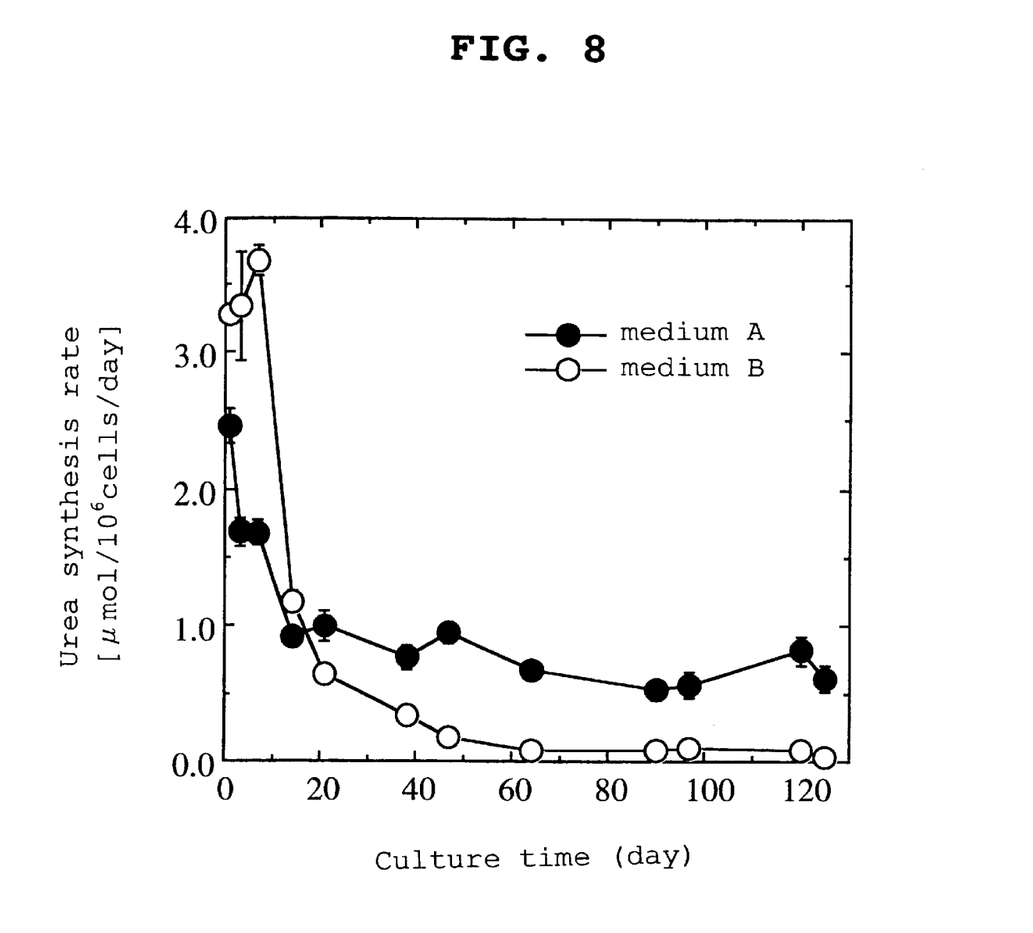
FIG. 8 shows the effect of the composition of the medium on the maintenance of the urea synthesis activity per unit cells of the centrifugation-derived hepatocyte multicellular aggregate of the present invention.
Figure 9:
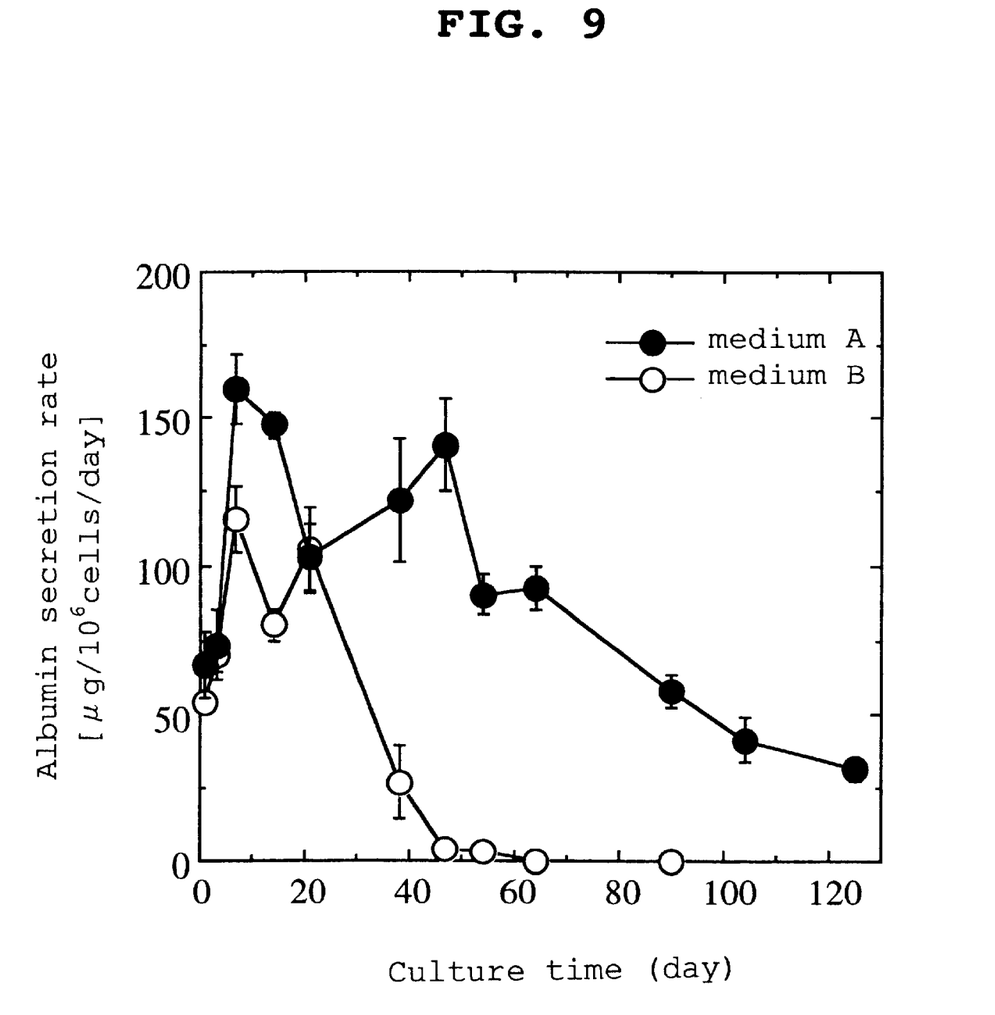
FIG. 9 shows the effect of the composition of the medium on the maintenance of the albumin secretion activity per unit cells of the centrifugation-derived hepatocyte multicellular aggregate of the present invention.

The changes in the ammonia metabolizing rate, urea synthesis rate and albumin secretion rate per unit cells are shown in FIG. 7, FIG. 8 and FIG. 9, respectively. When medium B was used, the ammonia metabolizing ability, urea synthesis ability and albumin secretion ability of the hepatocytes showed a rapid decrease with the progress of culture and disappeared in 4 to 5 weeks of culture. When medium A was used, hepatocytes retained fine activity of the above functions even in the 23rd week of culture, though lower than the initial activities.

From the foregoing, the culture of hepatocyte multicellular aggregate formed by centrifugal cell immobilization, in a culture medium containing DMEM supplemented with proline, EGF, hydrocortisone, selenious acid, linoleic acid, copper sulfate and zinc sulfate has been found to provide maintenance of high liver functions for a long period of at least 5 months.

This application is based on application Nos. 238818/1999 and 188275/2000 filed in Japan, the contents of which are incorporated hereinto by reference.

What is claimed is:

1. A module for cell culture comprising a structure comprising hollow fibers and at least two spacers, wherein the spacers have small pores regularly arranged therein and the hollow fibers pass through the small pores and are arranged regularly at a very small distance.

2. A hybrid artificial liver module comprising the module of claim 1 and hepatocytes immobilized therein.

3. A method for preparing a cell culture comprising immobilizing cells in a lumen of a hollow fiber, or a lumen or extra-fiber space of the module in a module for cell culture, by the use of a centrifugal force, and culturing the immobilized cells.

4. The method of claim 3, wherein the module comprises a structure comprising hollow fibers and at least two spacers, wherein the spacers have small pores regularly arranged therein and the hollow fibers pass through the small pores and are arranged regularly at a very small distance.

5. The method of claim 3, wherein the cells are hepatocytes.

6. A hybrid artificial liver module prepared according to the method of claim 5.

7. A medium comprising a Dulbecco's modified Eagle's medium as a basal medium, and proline, epidermal growth factor, insulin, hydrocortisone, selenious acid, linoleic acid, copper sulfate and zinc sulfate.

8. A medium comprising a mixed medium of Dulbecco's modified Eagle's medium and a different medium as a basal medium, and proline, epidermal growth factor, insulin, hydrocortisone, selenious acid, linoleic acid, copper sulfate and zinc sulfate.

9. The medium of claim 7, which cultures hepatocytes.

10. A module for cell culture comprising (a) a structure comprising hollow fibers and at least two spacers, wherein the spacers have small pores regularly arranged therein and the hollow fibers pass through the small pores and are arranged regularly at a very small distance, and (b) the medium of claim 7.

11. A method for preparing a cell culture comprising immobilizing cells in a lumen of a hollow fiber, or a lumen or extra-fiber space of the module in a module for cell culture, by the use of a centrifugal force, and culturing the immobilized cells using the medium of claim 7.

12. The method of claim 3, wherein the cells are cultured in a culture medium comprising a Dulbecco's modified Eagle's medium as a basal medium.

13. The method of claim 12, wherein the culture medium comprises a Dulbecco's modified Eagle's medium as a basal medium, and proline, epidermal growth factor, insulin, hydrocortisone, selenious acid, linoleic acid, copper sulfate and zinc sulfate.

14. The method of claim 3, wherein the cells are cultured in a culture medium comprising a Dulbecco's modified Eagle's medium and a different medium as a basal medium.

15. The method of claim 14, wherein the culture medium comprises a mixed medium of Dulbecco's modified Eagle's medium and a different medium as a basal medium, and proline, epidermal growth factor, insulin, hydrocortisone, selenious acid, linoleic acid, copper sulfate and zinc sulfate.

16. The medium of claim 8, which cultures hepatocytes.

17. A module for cell culture comprising (a) a structure comprising hollow fibers and at least two spacers, wherein the spacers have small pores regularly arranged therein and the hollow fibers pass through the small pores and are arranged regularly at a very small distance, and (b) the medium of claim 8.

18. A method for preparing a cell culture comprising immobilizing cells in a lumen of a hollow fiber, or a lumen or extra-fiber space of the module in a module for cell culture, by the use of a centrifugal force, and culturing the immobilized cells using the medium of claim 8.

19. The module of claim 1, wherein the spacers have pores about 20–100 $\mu$m greater than the diameter of the hollow fibers.

20. The module of claim 19, wherein the hollow fibers are arranged regularly at a distance of 20–1000 $\mu$m.

\* \* \* \* \*